United States Patent
Deane

(10) Patent No.: US 6,723,309 B1
(45) Date of Patent: Apr. 20, 2004

(54) HAIR CLEANSING CONDITIONER

(76) Inventor: Jeffrey Alan Deane, 6444 Fountain Ave., Hollywood, CA (US) 90028

( * ) Notice: Subject to any disclaimer, the term of this patent is extended or adjusted under 35 U.S.C. 154(b) by 117 days.

(21) Appl. No.: 10/166,460

(22) Filed: Jun. 10, 2002

(51) Int. Cl.[7] .............................. A61K 7/06; A61K 7/00; A61K 7/075; A61K 7/11

(52) U.S. Cl. ................ 424/70.1; 424/70.11; 424/70.13; 424/70.14; 424/74

(58) Field of Search ................................ 424/400, 70.1, 424/70.11, 70.13, 70.14, 74

(56) References Cited

U.S. PATENT DOCUMENTS 5,849,310 A * 12/1998 Trinh et al. .................. 424/401
6,190,678 B1 * 2/2001 Hasenoehrl et al. ........ 424/401

* cited by examiner

*Primary Examiner*—Gollamudi S. Kishore
*Assistant Examiner*—Simon J. Oh
(74) *Attorney, Agent, or Firm*—Norton R. Townsley; Belasco Jacobs & Townsley, LLP

(57) ABSTRACT

A hair cleanser comprising is a mixture of conditioners, cooling agents, emulsifiers, humectants, pH balancing agents, preservatives, thickeners, and vitamins. The cleanser may also include astringents, emollients, fragrances, re-fatting agents and botanicals.

16 Claims, No Drawings

HAIR CLEANSING CONDITIONER

BACKGROUND OF THE INVENTION

The present invention relates to the field of cosmetic treatments and more particularly to cleansers for the hair.

It is common practice nowadays to wash the hair with a shampoo and then to apply what is called a conditioner or conditioning treatment. The shampoo is a mixture of chemicals intended to remove dirt, oil and sweat from the hair and scalp. The chemicals used in shampoos are necessarily harsh removing essential oils and leaving the hair dry, dull and unmanageable. Shampoos frequently contain sodium lauryl sulfate. Conditioners or conditioning treatments are intended to replace the oils washed out of the hair by shampoos. It is the job of conditioners to make the cleaned hair shiny and manageable.

It does not make much sense to harshly cleanse hair so that essential oils are removed and then to replace these oils. It would make much better sense to utilize a hair cleanser that does not remove oils in the first place. Development of a hair cleanser which can clean the hair without removing essential oils represents a great improvement in the field of hair treatments and satisfies a long felt need of the public.

SUMMARY OF THE INVENTION

The present invention is a hair cleanser which cleanses the hair but does not remove essential oils. The hair cleanser of this invention comprises is a mixture of conditioners, cooling agents, emulsifiers, humectants, pH balancing agents, preservatives, thickeners, botanicals and vitamins. The invention may also include astringents, emollients, fragrances, and re-fatting agents. The preferred formulation is:

| | | |
|---|---|---|
| Glycerin | 2.00 to 5.00% | Humectant |
| Stearamidepropyl dimethyamine | 1.00% | Conditioner |
| Cetyl alcohol | 3.00% | Thickener |
| Panthenol | 0.03 to 0.25% | Vitamin |
| Trimethylsilylamodimethicone | 1.00% | Conditioner |
| Hydrolyzed whole wheat protein | 0.10% | Conditioner |
| PEG-60 almond glycerides | 0.00 to 0.10% | Re-fatting agent |
| Menthol | 0.10 to 0.30% | Cooling agent |
| Sweet almond oil | 0.00 to 0.20% | Emollient |
| Chamomile extract | 0.01 to 0.10% | Botanical |
| Calendula extract | 0.01 to 0.10% | Botanical |
| Citric acid | 0.01 to 0.01% | pH balance |
| Behetrimonium methosulfate | 1.80% | Conditioner |
| Cetearyl Alcohol | 1.65% | Thickener |
| Polysorbate 60 | 0.55% | Emulsifier |
| Tea Tree Leaf Oil | 0.00 to 0.30% | Fragrance |
| Rosemary Leaf Extract | 0.01 to 0.10% | Botanical |
| Wild cherry fruit extract | 0.01 to 0.10% | Botanical |
| Avocado Oil | 0.00 to 0.10% | Emollient |
| Olive Fruit Oil | 0.00 to 0.10% | Emollient |
| Aloe Vera Leaf Juice | 0.00 to 0.10% | Botanical |
| Methylchoroisothiazolinone | 0.02 to 0.03% | Preservative |
| Methyliosothiazolinone | 0.02% | Preservative |
| Fragrance (parfum) | 0.00 to 0.30% | Fragrance |
| Witch hazel | 0.00 to 5.00% | Astringent |
| Water | remainder to make 100% | |

Notes:
1) PEG stands for polyethylene glycol.
2) Panthenol is vitamin B5.

Notes: 1) PEG stands for polyethylene glycol.
2) Panthenol is vitamin B5.

The present invention does not contain harsh chemicals. Instead it can be thought of as a mixture of conditioners. It has been found experimentally that this invention cleanses the hair and leaves the hair shinier, with more body, and more manageable.

An appreciation of the other aims and objectives of the present invention and an understanding of it may be achieved by referring to the accompanying description of a preferred embodiment.

DETAILED DESCRIPTION OF THE PREFERRED EMBODIMENT

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

| | |
|---|---|
| 3.90% | conditioners |
| 0.10 to 0.30% | cooling agents |
| 0.55% | emulsifiers |
| 2.00 to 5.00% | humectants |
| 0.01% | pH balancing agent |
| 0.40 to 0.50% | preservatives |
| 0.01 to 0.10% | botanicals |
| 4.65% | thickeners |
| 0.03 to 0.25% | vitamins |

Conditioners help to make the hair more shiny and manageable. The cooling agent makes the formulation feel cool on the scalp. An emulsifier is a compound which helps to suspend water insoluble components of the formulation in small globules. A humectant is substance which absorbs or retains moisture; examples are glycerol, propylene glycol, and sorbitol. The pH balancing agent controls the pH of the formulation so that it will not bum the scalp or hair. A preservative is added to prevent breakdown of the formulation during storage. Botanicals are natural products which are believed to have efficacious effects on the body. The thickener is added to increase the viscosity of the formulation.

The formulation may also contain up to 5.00% astringent, up to 0.40% emollients, up to 0.60% fragrance and up to 0.10% re-fatting agents. An astringent is a compound that tends to contract or draw together organic tissues. An emollient is a compound that is softening or relaxing to the skin. The re-fatting agent tends to replace fat that is may have been previously stripped from the scalp and hair.

The preferred formulation for the present invention has the following formulation:

| | | |
|---|---|---|
| Glycerin | 2.00 to 5.00% | Humectant |
| Stearamidepropyl dimethyamine | 1.00% | Conditioner |
| Cetyl alcohol | 3.00% | Thickener |
| Panthenol | 0.03 to 0.25% | Vitamin |
| Trimethylsilylamodimethicone | 1.00% | Conditioner |
| Hydrolyzed whole wheat protein | 0.10% | Conditioner |
| PEG-60 almond glycerides | 0.00 to 0.10% | Re-fatting agent |
| Menthol | 0.10 to 0.30% | Cooling agent |
| Sweet almond oil | 0.00 to 0.20% | Emollient |
| Chamomile extract | 0.01 to 0.10% | Botanical |
| Calendula extract | 0.01 to 0.10% | Botanical |
| Citric acid | 0.01 to 0.01% | pH balance |
| Behetrimonium methosulfate | 1.80% | Conditioner |

-continued

| | | |
|---|---|---|
| Cetearyl Alcohol | 1.65% | Thickener |
| Polysorbate 60 | 0.55% | Emulsifier |
| Tea Tree Leaf Oil | 0.00 to 0.30% | Fragrance |
| Rosemary Leaf Extract | 0.01 to 0.10% | Botanical |
| Wild cherry fruit extract | 0.01 to 0.10% | Botanical |
| Avocado Oil | 0.00 to 0.10% | Emollient |
| Olive Fruit Oil | 0.00 to 0.10% | Emollient |
| Aloe Vera Leaf Juice | 0.00 to 0.10% | Botanical |
| Methylchoroisothiazolinone | 0.02 to 0.03% | Preservative |
| Methyliosothiazolinone | 0.02% | Preservative |
| Fragrance (parfum) | 0.00 to 0.30% | Fragrance |
| Witch hazel | 0.00 to 5.00% | Astringent |
| Water | remainder to make 100% | |

Hydrolyzed wheat protein is a naturally derived protein that contains wheat oligosaccharides (carbohydrates) and constitutes a unique hydrating complex offering a combination of moisture-balancing and film-forming properties that work synergistically to give hair better body control, and skin, a smoother softer feel.

Aloe vera is included in the formulation for its cleansing properties. It cools the skin and conditions the hair. Glycerin is has soothing and moisturizing effects. The panthenol is a moisture balancer. The trimethylsilylamodimethicone adds sheen and shine to the hair. The menthol has stimulating, cooling and cleansing effects and increases blood circulation. The sweet almond oil is very moisturizing and works effectively on all skin types. The rosemary extract has anti-bacterial properties and cleans very effectively. The isothiazolinones are biocides which prevent spoilage of the product.

Samples of the above formulation were used experimentally on clients' hair at a hair dressing salon in the Hollywood area for a some months prior to the submission of this application. Some clients knew that an experimental hair cleansing formulation was being used while others did not. All hair was cleansed as effectively as if a shampoo was used. Clients were uniform in their praise of the effect of this cleanser on their hair. They found that their hair was left shinier, more manageable and with more body that with other shampoo/conditioner combinations they had used. Many wanted to know what the formulation was and when it would be commercially available.

The hair cleanser formulation provided above replaces shampoos and conditioners. The formulation does not contain sodium lauryl sulfate, detergents or other harsh chemicals. When used it does not remove natural oils from the hair and scalp. It does not remove color or dry out the hair.

EXAMPLES

The following formulations, having the indicated fragrances, were made for testing:

| | Tea Tree | Sweet almond mint | Cucumber Aloe | Vanilla Almond | Fig | Pomegranate | Lavender |
|---|---|---|---|---|---|---|---|
| Glycerin | 5.00 | 4.00 | 2.00 | 4.00 | 4.00 | 4.00 | 4.00 |
| Stearamidepropyl dimethyamine | 1.00 | 1.00 | 1.00 | 1.00 | 1.00 | 1.00 | 1.00 |
| Cetyl alcohol | 3.00 | 3.00 | 3.00 | 3.00 | 3.00 | 3.00 | 3.00 |
| Panthenol | 0.25 | 0.25 | 0.03 | 0.25 | 0.25 | 0.25 | 0.25 |
| Trimethylsilylamodimethicone | 1.00 | 1.00 | 1.00 | 1.00 | 1.00 | 1.00 | 1.00 |
| Hydrolyzed whole wheat protein | 0.10 | 0.10 | 0.10 | 0.10 | 0.10 | 0.10 | 0.10 |
| PEG-60 almond glycerides | 0.10 | 0.10 | 0.10 | 0.10 | 0.10 | 0.10 | 0.00 |
| Menthol | 0.30 | 0.10 | 0.30 | 0.30 | 0.30 | 0.30 | 0.10 |
| Sweet almond oil | 0.20 | 0.20 | 0.00 | 0.20 | 0.20 | 0.20 | 0.20 |
| Chamomile extract | 0.10 | 0.10 | 0.01 | 0.10 | 0.10 | 0.10 | 0.10 |
| Calendula extract | 0.10 | 0.10 | 0.01 | 0.10 | 0.10 | 0.10 | 0.10 |
| Citric acid | 0.01 | 0.01 | 0.01 | 0.01 | 0.01 | 0.01 | 0.01 |
| Behetrimonium methosulfate | 1.80 | 1.80 | 1.80 | 1.80 | 1.80 | 1.80 | 1.80 |
| Cetearyl Alcohol | 1.65 | 1.65 | 1.65 | 1.65 | 1.65 | 1.65 | 1.65 |
| Polysorbate 60 | 0.55 | 0.55 | 0.55 | 0.55 | 0.55 | 0.55 | 0.55 |
| Tea Tree Leaf Oil | 0.30 | 0.00 | 0.00 | 0.00 | 0.00 | 0.00 | 0.00 |
| Rosemary Leaf Extract | 0.10 | 0.10 | 0.01 | 0.10 | 0.10 | 0.10 | 0.01 |
| Wild cherry fruit extract | 0.10 | 0.10 | 0.01 | 0.10 | 0.10 | 0.10 | 0.10 |
| Avocado Oil | 0.10 | 0.00 | 0.00 | 0.00 | 0.00 | 0.00 | 0.00 |
| Olive Fruit Oil | 0.10 | 0.00 | 0.00 | 0.00 | 0.00 | 0.00 | 0.00 |
| Aloe Vera Leaf Juice | 0.10 | 0.00 | 0.10 | 0.00 | 0.00 | 0.00 | 0.00 |
| Methylchoroisothiazolinone | 0.02 | 0.03 | 0.03 | 0.03 | 0.03 | 0.03 | 0.03 |
| Methyliosothiazolinone | 0.02 | 0.02 | 0.02 | 0.02 | 0.02 | 0.02 | 0.02 |
| Fragrance (parfum) | 0.30 | 0.00 | 0.20 | 0.30 | 0.30 | 0.25 | 0.25 |
| Witch hazel | 0.00 | 0.00 | 5.00 | 0.00 | 0.00 | 0.00 | 0.00 |
| Water | 83.70 | 85.79 | 83.07 | 85.29 | 85.29 | 85.34 | 85.73 |

It will be understood by those familiar with the art to which this invention pertains that it is impossible to create things to a precise measure. There is always some tolerance introduced by the device used for measuring and the human being who does the measuring. For example it is impossible to add exactly 1 liter of a chemical to a mixture. So throughout the specification and claims of this document, it will be understood that where a single figure is shown in a formulation or list of ingredients there will always be some tolerance on this figure. For the purposes of this document the tolerance will be assumed to be ±10%.

Thus, the present invention has been described herein with reference to a particular embodiment for a particular application. Those having ordinary skill in the art and access to the present teachings will recognize additional modifications, applications and embodiments within the scope thereof.

It is therefore intended by the appended claims to cover any and all such applications, modifications and embodiments within the scope of the present invention. The hair cleanser has been described with reference to a particular embodiment. Other modifications and enhancements can be made without departing from the spirit and scope of the claims that follow.

What is claimed is:

1. A hair cleanser comprising:

| | |
|---|---|
| 2.00 to 5.00% | glycerin, |
| 1.00% | stearamidepropyl dimethyamine, |
| 3.00% | cetyl alcohol, |
| 0.03 to 0.25% | panthenol, |
| 1.00% | trimethylsilylamodimethicone, |
| 0.10% | hydrolyzed whole wheat protein, |
| 0.00 to 0.10% | PEG-60 almond glycerides, |
| 0.10 to 0.30% | menthol, |
| 0.00 to 0.20% | sweet almond oil, |
| 0.01 to 0.10% | chamomile extract, |
| 0.01 to 0.10% | calendula extract, |
| 0.01 to 0.01% | citric acid, |
| 1.80% | behetrimonium methosulfate, |
| 1.65% | cetearyl Alcohol, |
| 0.55% | polysorbate 60, |
| 0.00 to 0.30% | tea tree leaf oil, |
| 0.01 to 0.10% | rosemary leaf extract, |
| 0.01 to 0.10% | wild cherry fruit extract, |
| 0.00 to 0.10% | avocado oil, |
| 0.00 to 0.10% | olive fruit oil, |
| 0.00 to 0.10% | aloe vera leaf juice, |
| 0.02 to 0.03% | methylchoroisothiazolinone, |
| 0.02% | methyliosothiazolinone, |
| 0.00 to 0.30% | fragrance, |
| 0.00 to 5.00% | witch hazel, and |
| remainder to make 100% | water. |

2. A method of formulating a hair cleanser comprising the steps of:

a) obtaining the following ingredients:
glycerin,
stearamidepropyl dimethyamine,
cetyl alcohol,
panthenol,
trimethylsilylamodimethicone,
hydrolyzed whole wheat protein,
PEG-60 almond glycerides,
menthol,
sweet almond oil,
chamomile extract,
calendula extract,
citric acid,
behetrimonium methosulfate,
cetearyl alcohol,
polysorbate 60,
tea tree leaf oil,
rosemary leaf extract,
wild cherry fruit extract,
avocado oil,
olive fruit oil,
aloe vera leafjuice,
methylchoroisothiazolinone,
methyliosothiazolinone,
fragrance,
witch hazel, and
water; and b) mixing said ingredients in the following proportions

| | |
|---|---|
| 2.00 to 5.00% | glycerin, |
| 1.00% | stearamidepropyl dimethyamine, |
| 3.00% | cetyl alcohol, |
| 0.03 to 0.25% | panthenol, |
| 1.00% | trimethylsilylamodimethicone, |
| 0.10% | hydrolyzed whole wheat protein, |
| 0.00 to 0.10% | PEG-60 almond glycerides, |
| 0.10 to 0.30% | menthol, |
| 0.00 to 0.20% | sweet almond oil, |
| 0.01 to 0.10% | chamomile extract, |
| 0.01 to 0.10% | calendula extract, |
| 0.01 to 0.01% | citric acid, |
| 1.80% | behetrimonium methosulfate, |
| 1.65% | cetearyl alcohol, |
| 0.55% | polysorbate 60, |
| 0.00 to 0.30% | tea tree leaf oil, |
| 0.01 to 0.10% | rosemary leaf extract, |
| 0.01 to 0.10% | wild cherry fruit extract, |
| 0.00 to 0.10% | avocado oil, |
| 0.00 to 0.10% | olive fruit oil, |
| 0.00 to 0.10% | aloe vera leaf juice, |
| 0.02 to 0.03% | methylchoroisothiazolinone, |
| 0.02% | methyliosothiazolinone, |
| 0.00 to 0.30% | fragrance, |
| 0.00 to 5.00% | witch hazel, and |
| remainder to make 100% | water. |

3. A hair cleanser comprising: a conditioner selected from the group consisting of stearamidepropyl dimethyamine, trimethylsilylamodimethicone, hydrolyzed whole wheat protein, behetrimonium methosulfate, and mixtures thereof; a cooling agent; an emulsifier; a humectant; a pH balancing agent; a preservative selected from the group consisting of methylchoroisothiazolinone, methyliosothiazolinone and mixtures thereof; a thickener selected from the group consisting of cetyl alcohol, cetearyl alcohol and mixtures thereof; a botanical is selected from the group consisting of chamomile extract, calendula extract, rosemary leaf extract, wild cherry fruit extract, aloe vera leaf juice and mixtures thereof; and a vitamin.

4. A hair cleanser as claimed in claim 3 in which said cooling agent is menthol.

5. A hair cleanser as claimed in claim 3 in which said emulsifier is Polysorbate 60.

6. A hair cleanser as claimed in claim 3 in which said humectant is glycerin.

7. A hair cleanser as claimed in claim 3 in which said pH balancing agent is citric acid.

8. A hair cleanser as claimed in claim 3 in which said vitamin is panthenol.

9. A hair cleanser as claimed in claim 3 further comprising an astringent.

10. A hair cleanser as claimed in claim 9 in which said astringent is witch hazel.

11. A hair cleanser as claimed in claim 3 further comprising an emollient.

12. A hair cleanser as claimed in claim 11 in which said emollient is selected from the group consisting of menthol, sweet almond oil, avocado oil, olive fruit oil and mixtures thereof.

13. A hair cleanser as claimed in claim 3 further comprising a fragrance.

14. A hair cleanser as claimed in claim 13 in which said fragrance is tea tree leaf oil.

15. A hair cleanser as claimed in claim 3 further comprising a re-fatting agent.

16. A hair cleanser as claimed in claim 15 in which said re-fatting agent is PEG-60 almond glycerides.

* * * * *